US012303331B2

United States Patent
Matsumoto

(10) Patent No.: US 12,303,331 B2
(45) Date of Patent: May 20, 2025

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Tsuyoshi Matsumoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 384 days.

(21) Appl. No.: 17/553,234

(22) Filed: Dec. 16, 2021

(65) Prior Publication Data

US 2022/0104791 A1 Apr. 7, 2022

Related U.S. Application Data

(63) Continuation of application No. PCT/JP2020/021894, filed on Jun. 3, 2020.

(30) Foreign Application Priority Data

Jul. 23, 2019 (JP) ................. 2019-135415

(51) Int. Cl.
*A61B 8/00* (2006.01)
*A61B 8/08* (2006.01)

(52) U.S. Cl.
CPC ............ *A61B 8/4245* (2013.01); *A61B 8/085* (2013.01); *A61B 8/0858* (2013.01);
(Continued)

(58) Field of Classification Search
CPC ......... A61B 8/08; A61B 8/085; A61B 8/0858; A61B 8/4245; A61B 8/4281; A61B 8/429; A61B 8/4488; A61B 8/54; A61B 8/565

See application file for complete search history.

(56) References Cited

U.S. PATENT DOCUMENTS

2007/0093716 A1\* 4/2007 Radulescu ............ G01S 7/5206
  600/437
2008/0269605 A1 10/2008 Nakaya
(Continued)

FOREIGN PATENT DOCUMENTS

DE 102017221330 A1 \* 5/2019 ........... A61B 5/0053
JP 2005-110724 A 4/2005
(Continued)

OTHER PUBLICATIONS

Translated Baumann DE102017221330 (Year: 2017).\*
(Continued)

*Primary Examiner* — Anne M Kozak
*Assistant Examiner* — Brooke Lyn Klein
(74) *Attorney, Agent, or Firm* — Studebaker Brackett PLLC

(57) ABSTRACT

An ultrasound diagnostic apparatus (1) includes a gel layer thickness calculation unit (9) that calculates a thickness of a gel layer by analyzing an ultrasound image; a tissue recognition unit (10) that recognizes a tissue of a subject by analyzing the ultrasound image; and a press state determination unit (11) that determines a press state of an ultrasound probe (21) against a body surface of the subject on the basis of a shape change of the tissue recognized by the tissue recognition unit (10) in a case where the calculated thickness of the gel layer is equal to or less than a thickness threshold value.

8 Claims, 7 Drawing Sheets

(52) U.S. Cl.
CPC ............ *A61B 8/4281* (2013.01); *A61B 8/429* (2013.01); *A61B 8/4488* (2013.01); *A61B 8/54* (2013.01)

(56) References Cited

U.S. PATENT DOCUMENTS

| | | | | |
|---|---|---|---|---|
| 2008/0269606 | A1* | 10/2008 | Matsumura | A61B 8/12 382/128 |
| 2009/0203997 | A1* | 8/2009 | Ustuner | G01S 7/52071 600/443 |
| 2011/0040187 | A1* | 2/2011 | Matsumura | A61B 5/6843 600/443 |
| 2014/0305218 | A1* | 10/2014 | Chang | G01N 29/11 73/620 |
| 2015/0057545 | A1* | 2/2015 | Takagi | G06T 7/0012 600/443 |

FOREIGN PATENT DOCUMENTS

| | | |
|---|---|---|
| JP | 2008-272025 A | 11/2008 |
| JP | 2011-072522 A | 4/2011 |
| JP | 2015029610 A * | 2/2015 |
| JP | 2015-061591 A | 4/2015 |
| WO | WO-2013041992 A1 * | 3/2013 ........... A61B 8/4281 |

OTHER PUBLICATIONS

Translated Horie JP2015029610 (Year: 2015).*
International Search Report issued in PCT/JP2020/021894; mailed Aug. 18, 2020.
International Preliminary Report on Patentability and Written Opinion issued in PCT/JP2020/021894; issued Jan. 25, 2022.
Csurka et al.: Visual Categorization with Bags of Keypoints, Proc. of ECCV Workshop on Statistical Learning in Computer Vision, pp. 1-16, (2004).
Krizhevsky et al.: ImageNet Classification with Deep Convolutional Neural Networks, Advances in Neural Information Processing Systems 25, pp. 1-9, (2012).

* cited by examiner

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2020/021894 filed on Jun. 3, 2020, which claims priority under 35 U.S.C. § 119(a) to Japanese Patent Application No. 2019-135415 filed on Jul. 23, 2019. The above application is hereby expressly incorporated by reference, in its entirety, into the present application.

BACKGROUND OF THE INVENTION

1. Field of the Invention

The present invention relates to an ultrasound diagnostic apparatus, and a control method of the ultrasound diagnostic apparatus which acquire an ultrasound image of the inside of a subject through a gel layer applied to a body surface of the subject.

2. Description of the Related Art

In the related art, an ultrasound diagnostic apparatus has been known as an apparatus for obtaining an image of the inside of a subject. The ultrasound diagnostic apparatus generally comprises an ultrasound probe comprising a transducer array in which a plurality of ultrasonic transducers are arranged. In a state where the ultrasound probe is in contact with the body surface of the subject, an ultrasound beam is transmitted toward the inside of the subject from the transducer array and an ultrasound echo from the subject is received by the transducer array so that an electric signal corresponding to the ultrasound echo is acquired. Further, the ultrasound diagnostic apparatus electrically processes the obtained electric signal to generate an ultrasound image of the corresponding site of the subject.

Here, it is known that a tissue such as a vein present in the subcutaneous portion of the subject is easily deformed by external pressure. Therefore, in a case where such a tissue is observed by the ultrasound diagnostic apparatus, in order to prevent the tissue from being deformed by the pressing of the ultrasound probe against the body surface of the subject, for example, a procedure is generally performed in which a gel layer for so-called ultrasonography is applied to the body surface of the subject, and the tissue is observed without pressing the ultrasound probe against the body surface of the subject while the ultrasound probe is in contact with the applied gel layer. However, the body surface of the subject may be pressed by the ultrasound probe in a case where the operator concentrates on searching for the tissue as an observation target.

Thus, in order to prevent the pressing against the body surface of the subject by the ultrasound probe, for example, an ultrasound diagnostic apparatus that encourages the operator to perform an appropriate procedure, as disclosed in JP2015-061591A has been developed. The ultrasound diagnostic apparatus in JP2015-061591A determines whether a positional relationship between the ultrasound probe and an observation target site is appropriate on the basis of the thickness of the gel layer applied to the body surface of the subject.

SUMMARY OF THE INVENTION

By the way, it is known that the gel layer applied to the body surface of the subject gradually becomes thinner in a case where the ultrasound probe is moved on the gel layer by the operator even in a state where the ultrasound probe does not press the body surface of the subject. Since the ultrasound diagnostic apparatus in JP2015-061591A determines whether the positional relationship between the ultrasound probe and the observation target site is appropriate on the basis of only the thickness of the gel layer, the ultrasound diagnostic apparatus may detect that the gel layer has become thinner to erroneously determine that the ultrasound probe is pressing the body surface of the subject even in a case where the ultrasound probe is not pressing the body surface of the subject.

The present invention has been made in order to solve such a problem in the related art, and an object thereof is to provide an ultrasound diagnostic apparatus which can accurately determine a press state of the ultrasound probe against the body surface of the subject and a control method of the ultrasound diagnostic apparatus.

In order to achieve the object, an ultrasound diagnostic apparatus according to an aspect of the present invention is an ultrasound diagnostic apparatus that acquires an ultrasound image by bringing an ultrasound probe into contact with a gel layer applied to a body surface of a subject, the ultrasound diagnostic apparatus comprising the ultrasound probe including at least a transducer array; a transmission and reception circuit that causes the transducer array to transmit an ultrasound beam toward the subject, and processes a reception signal output from the transducer array that has received an ultrasound echo from the subject to generate a sound ray signal; an image generation unit that generates the ultrasound image on the basis of the sound ray signal generated by the transmission and reception circuit; a gel layer thickness calculation unit that calculates a thickness of the gel layer by analyzing the ultrasound image generated by the image generation unit; a tissue recognition unit that recognizes a tissue of the subject by analyzing the ultrasound image generated by the image generation unit; and a press state determination unit that determines a press state of the ultrasound probe against the body surface of the subject on the basis of a shape change of the tissue recognized by the tissue recognition unit in a case where the thickness of the gel layer calculated by the gel layer thickness calculation unit is equal to or less than a thickness threshold value.

It is preferable that in a case where a shape change degree representing the shape change of the tissue recognized by the tissue recognition unit exceeds a shape change degree threshold value, the press state determination unit determines that the body surface of the subject is pressed by the ultrasound probe, and in a case where the shape change degree of the tissue recognized by the tissue recognition unit is equal to or less than the shape change degree threshold value, the press state determination unit determines that the body surface of the subject is not pressed by the ultrasound probe.

Further, it is preferable that the ultrasound diagnostic apparatus comprises a notification unit that instructs an operator to stop pressing by the ultrasound probe in a case where the press state determination unit determines that the body surface of the subject is pressed, and instructs the operator to replenish a gel of the gel layer in a case where the press state determination unit determines that the body surface of the subject is not pressed.

The tissue recognition unit may recognize at least one of the body surface, a blood vessel, or a subcutaneous anatomical structure other than the blood vessel, as the tissue.

Further, the tissue recognition unit may recognize a blood vessel as the tissue, and the press state determination unit may set the shape change degree threshold value such that the shape change degree threshold value is increased as a position of the blood vessel recognized by the tissue recognition unit is shallower.

The thickness threshold value may be a predetermined value.

Alternatively, the press state determination unit may set a value obtained by multiplying the thickness of the gel layer, which is first calculated by the gel layer thickness calculation unit, by a certain ratio as the thickness threshold value.

A control method of an ultrasound diagnostic apparatus according to another aspect of the present invention comprises causing a transducer array of an ultrasound probe brought into contact with a gel layer applied to a body surface of a subject to transmit an ultrasound beam toward the subject, and processing a reception signal output from the transducer array that has received an ultrasound echo from the subject to generate a sound ray signal; generating an ultrasound image on the basis of the generated sound ray signal; calculating a thickness of the gel layer by analyzing the generated ultrasound image; recognizing a tissue of the subject by analyzing the generated ultrasound image; and determining a press state of the ultrasound probe against the body surface of the subject on the basis of a shape change of the recognized tissue in a case where the calculated thickness of the gel layer is equal to or less than a thickness threshold value.

According to the present invention, there are provided the image generation unit that generates the ultrasound image; the gel layer thickness calculation unit that calculates the thickness of the gel layer by analyzing the ultrasound image generated by the image generation unit; the tissue recognition unit that recognizes the tissue of the subject by analyzing the ultrasound image generated by the image generation unit; and the press state determination unit that determines the press state of the ultrasound probe against the body surface of the subject on the basis of the shape change of the tissue recognized by the tissue recognition unit in a case where the thickness of the gel layer calculated by the gel layer thickness calculation unit is equal to or less than the thickness threshold value, and therefore, it is possible to accurately determine the press state of the ultrasound probe against the body surface of the subject.

DESCRIPTION OF THE PREFERRED EMBODIMENTS

Hereinafter, embodiments of the invention will be described with reference to the accompanying drawings.

The description of configuration requirements described below is given on the basis of the representative embodiment of the present invention, but the present invention is not limited to such an embodiment.

In the present specification, a numerical range represented using "to" means a range including the numerical values before and after "to" as a lower limit value and an upper limit value.

In addition, in the present specification, the terms "perpendicular" and "parallel" include a range of errors allowed in the technical field to which the present invention belongs. For example, the terms "perpendicular" and "parallel" mean a range less than ±10 degrees with respect to the strict perpendicular or parallel, and the error with respect to the strict perpendicular or parallel is preferably 5 degrees or less, and more preferably 3 degrees or less.

In the present specification, the terms "same" and "identical" include an error range generally allowed in the technical field. Further, in the present specification, in a case of referring to "all", "any", or "whole surface", the term includes an error range generally allowed in the technical field in addition to a case of 100%, and includes, for example, a case of 99% or more, a case of 95% or more, or a case of 90% or more.

First Embodiment

Figure 1:
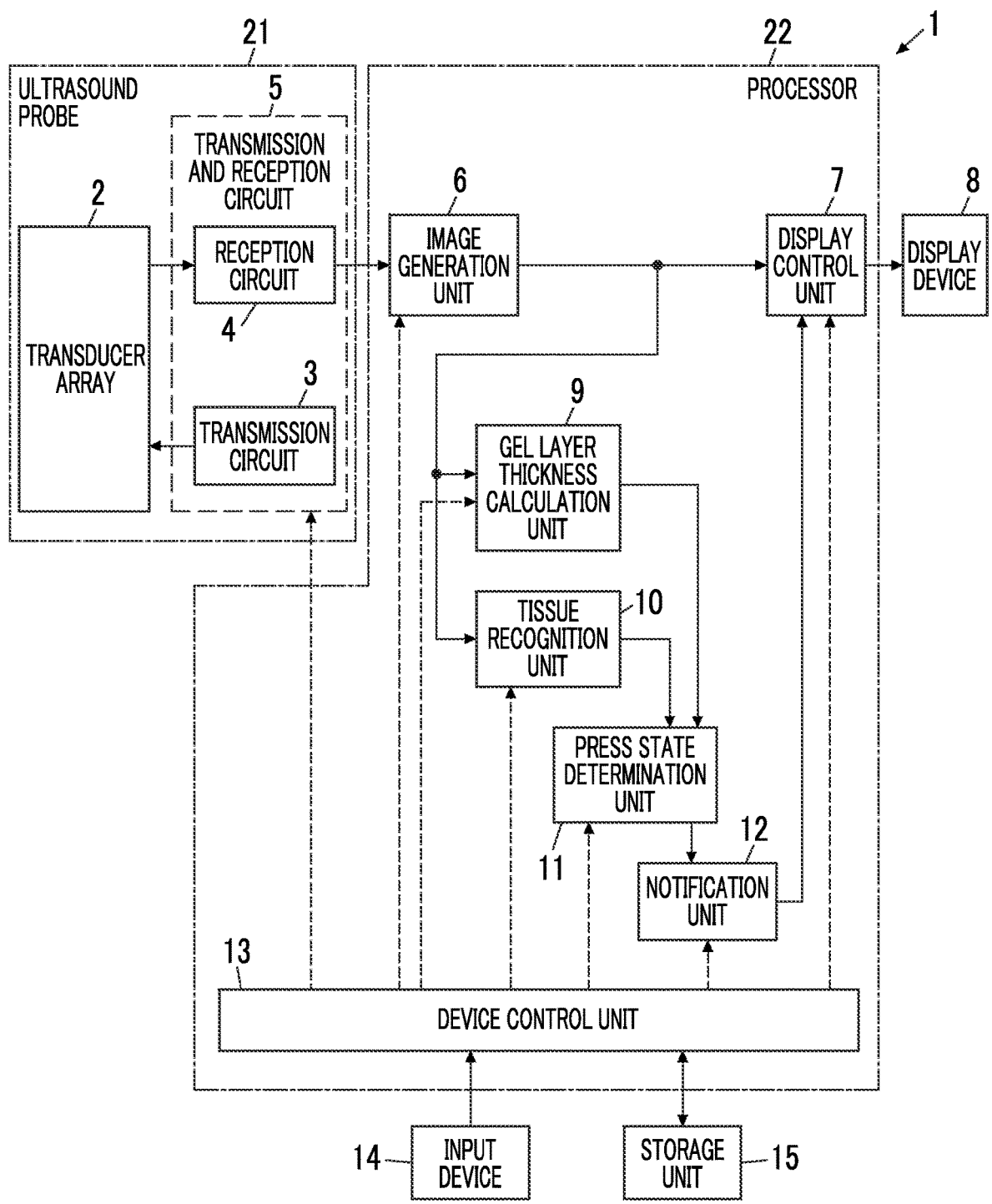
FIG. 1 is a block diagram illustrating a configuration of an ultrasound diagnostic apparatus according to a first embodiment of the present invention.

FIG. 1 illustrates a configuration of an ultrasound diagnostic apparatus 1 according to a first embodiment of the present invention. The ultrasound diagnostic apparatus 1 comprises a transducer array 2, and each of a transmission circuit 3 and a reception circuit 4 is connected to the transducer array 2. Here, the transmission circuit 3 and the reception circuit 4 constitute a transmission and reception circuit 5. An image generation unit 6, a display control unit 7, and a display device 8 are sequentially connected to the reception circuit 4. A gel layer thickness calculation unit 9 and a tissue recognition unit 10 are connected to the image generation unit 6, and a press state determination unit 11 is connected to the gel layer thickness calculation unit 9 and the tissue recognition unit 10. A notification unit 12 is connected to the press state determination unit 11, and the display control unit 7 is connected to the notification unit 12.

Further, a device control unit 13 is connected to the transmission and reception circuit 5, the image generation unit 6, the display control unit 7, the gel layer thickness calculation unit 9, the tissue recognition unit 10, the press state determination unit 11, and the notification unit 12. An input device 14 and a storage unit 15 are connected to the device control unit 13. The device control unit 13 and the storage unit 15 are connected so as to exchange information bidirectionally.

The transducer array 2 and the transmission and reception circuit 5 are included in an ultrasound probe 21. Further, the image generation unit 6, the display control unit 7, the gel layer thickness calculation unit 9, the tissue recognition unit 10, the press state determination unit 11, the notification unit 12, and the device control unit 13 constitute a processor 22 for the ultrasound diagnostic apparatus 1.

The transducer array 2 of the ultrasound probe 21 illustrated in FIG. 1 has a plurality of transducers arranged in a one-dimensional or two-dimensional manner. According to a drive signal supplied from the transmission circuit 3, each of the transducers transmits an ultrasonic wave and receives an ultrasound echo from a subject to output a signal based on the ultrasound echo. For example, each transducer is configured by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The transmission circuit 3 includes, for example, a plurality of pulse generators, and the transmission circuit 3 adjusts the amount of delay of each drive signal so that ultrasonic waves transmitted from the plurality of transducers of the transducer array 2 form an ultrasound beam on the basis of a transmission delay pattern selected according to the control signal from the device control unit 13, and supplies the obtained signals to the plurality of transducers. Thus, in a case where a pulsed or continuous-wave voltage is applied to the electrodes of the transducers of the transducer array 2, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and propagates toward the transducer array 2 of the ultrasound probe 21. The ultrasound echo propagating toward the transducer array 2 in this manner is received by each transducer constituting the transducer array 2. In this case, each transducer constituting the transducer array 2 expands and contracts by receiving the propagating ultrasound echo to generate electric signals, and outputs the electrical signals to the reception circuit 4.

Figure 2:
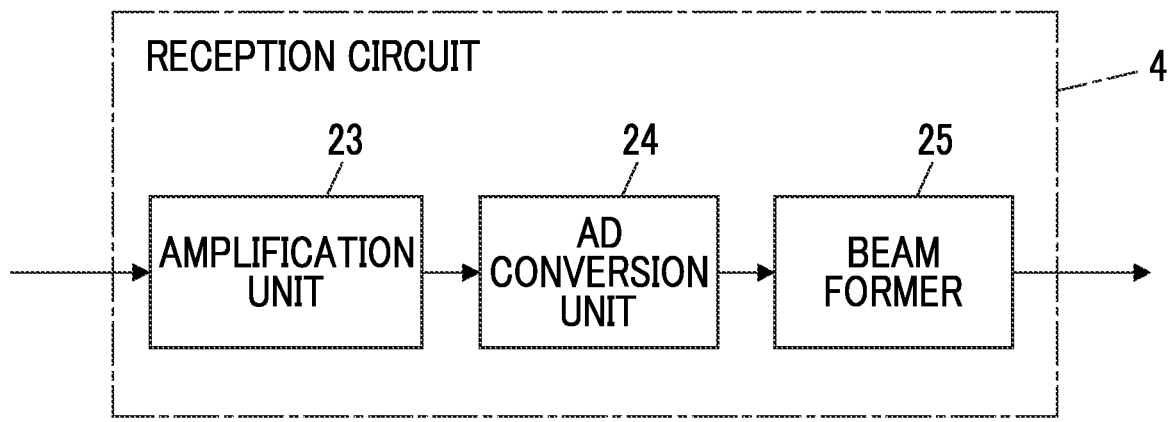
FIG. 2 is a block diagram illustrating an internal configuration of a reception circuit in the first embodiment of the present invention.

The reception circuit 4 processes the signal output from the transducer array 2 according to the control signal from the device control unit 13, and generates a sound ray signal. As illustrated in FIG. 2, the reception circuit 4 has a configuration in which an amplification unit 23, an analog digital (AD) conversion unit 24, and a beam former 25 are connected in series.

The amplification unit 23 amplifies the signal input from each transducer constituting the transducer array 2, and transmits the amplified signal to the AD conversion unit 24. The AD conversion unit 24 converts the signal transmitted from the amplification unit 23 into digital reception data, and transmits the reception data to the beam former 25. The beam former 25 performs so-called reception focusing processing in which addition is performed by giving delays to respective pieces of the reception data converted by the AD conversion unit 24 according to a sound speed distribution or a sound speed set on the basis of a reception delay pattern selected according to the control signal from the device control unit 13. Through the reception focusing processing, a sound ray signal in which each piece of the reception data converted by the AD conversion unit 24 is phased and added and the focus of the ultrasound echo is narrowed is acquired.

Figure 3:
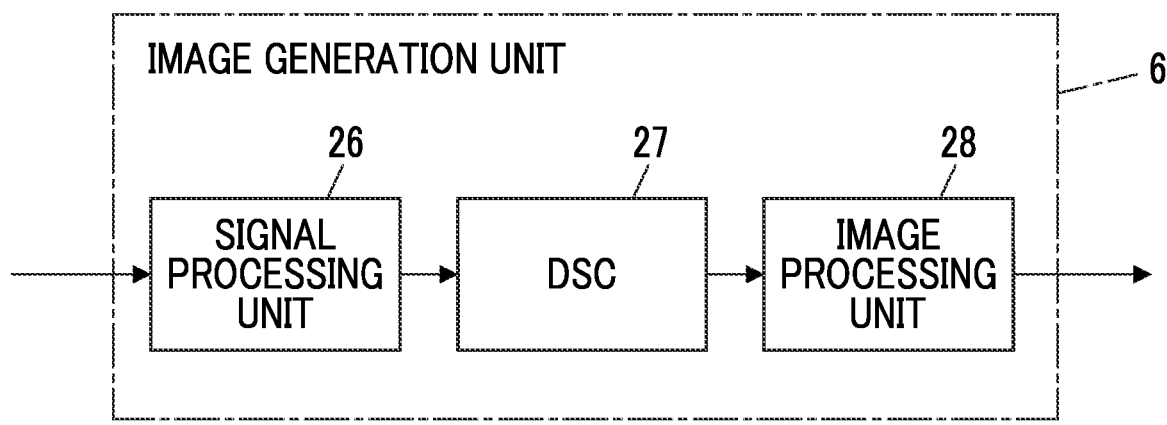
FIG. 3 is a block diagram illustrating an internal configuration of an image generation unit in the first embodiment of the present invention.

As illustrated in FIG. 3, the image generation unit 6 has a configuration in which a signal processing unit 26, a digital scan converter (DSC) 27, and an image processing unit 28 are sequentially connected in series.

The signal processing unit 26 generates a B-mode image signal, which is tomographic image information regarding tissues inside the subject, by performing, on the sound ray signal generated by the reception circuit 4, correction of the attenuation due to the distance according to the depth of the reflection position of the ultrasonic wave and then performing envelope detection processing.

The DSC 27 converts (raster conversion) the B-mode image signal generated by the signal processing unit 26 into an image signal according to a normal television signal scanning method.

The image processing unit 28 performs various kinds of necessary image processing such as gradation processing on the B-mode image signal input from the DSC 27, and then outputs the B-mode image signal to the display control unit 7, the gel layer thickness calculation unit 9, and the tissue recognition unit 10. In the following, the B-mode image signal subjected to the image processing by the image processing unit 28 is simply referred to as an ultrasound image.

In a case where a tissue such as a veins that is easily deformed by external pressure is observed, in order to prevent the tissue from being deformed by the pressing of the ultrasound probe against the body surface of the subject, a procedure is generally performed in which a gel layer for so-called ultrasonography is applied to the body surface of the subject, and the tissue is observed without pressing the ultrasound probe against the body surface of the subject while the ultrasound probe is in contact with the applied gel layer.

Here, the gel layer is composed of a highly viscous liquid such as a so-called polymer-absorbing gel. In general, the reflection and attenuation of the ultrasonic waves are likely to occur in a case where an air layer is present between the ultrasound probe and the body surface of the subject, but the gel layer can sufficiently transmit the ultrasonic waves and fill the gap between the body surface of the subject and the ultrasound probe, and therefore it is possible to reduce the reflection and attenuation of the ultrasonic waves between the ultrasound probe and the body surface of the subject.

Figure 4:
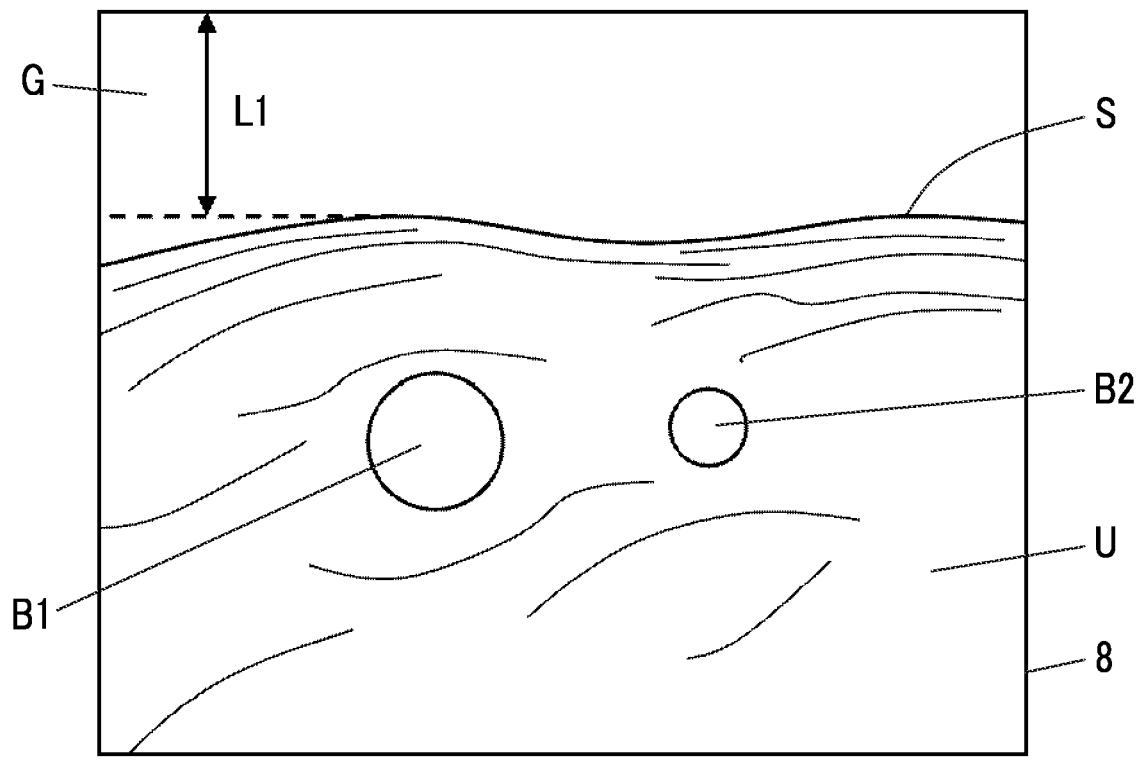
FIG. 4 is a schematic diagram of an ultrasound image in a state where a gel layer is thicker than a thickness threshold value and a body surface of a subject is not pressed by an ultrasound probe, in the first embodiment of the present invention.

The gel layer thickness calculation unit 9 analyzes the ultrasound image generated by the image generation unit 6 to calculate the thickness of the gel layer applied to the body surface of the subject. For example, as illustrated in FIG. 4, the gel layer thickness calculation unit 9 recognizes a body surface S of the subject in an ultrasound image U, and calculates the shallowest position of the ultrasound image U in a depth direction of the ultrasound image U, that is, the shortest length from the upper end portion of the ultrasound image U to the body surface S, as a thickness L1 of a gel layer G.

Here, since the reflection of the ultrasonic waves is unlikely to occur inside the gel layer G, the gel layer G has low brightness in the ultrasound image U. On the other hand, since the reflection of the ultrasonic waves is likely to occur in a boundary portion between the gel layer G and the body surface S of the subject, the boundary portion has high brightness in the ultrasound image U. Therefore, the gel layer thickness calculation unit 9 can recognize a place where a brightness change in the depth direction from the shallow portion of the ultrasound image U is greater than a certain value, as the body surface S, and calculate the shortest length from the upper end portion of the ultrasound image U to the recognized body surface S as the thickness L1 of the gel layer G. The gel layer thickness calculation unit 9 can use, for example, a known algorithm when recognizing the body surface S on the ultrasound image U. For example, the gel layer thickness calculation unit 9 can store typical pattern data of the body surface S in advance as a template, calculate a similarity degree for the pattern data while searching the ultrasound images U using the template, and consider that the body surface S is present in a place where the similarity degree is equal to or greater than a threshold value and is the maximum.

The gel layer thickness calculation unit 9 can calculate the thickness of the gel layer G indirectly by obtaining the deep position of the body surface S, which is recognized in this manner, in the ultrasound image U.

Further, for the calculation of the similarity degree, in addition to simple template matching, for example, a machine learning method described in Csurka et al.: Visual Categorization with Bags of Keypoints, Proc. of ECCV Workshop on Statistical Learning in Computer Vision, pp. 59-74 (2004) or a general image recognition method using deep learning described in Krizhevsk et al.: ImageNet Classification with Deep Convolutional Neural Networks, Advances in Neural Information Processing Systems 25, pp. 1106-1114 (2012) can be used.

The tissue recognition unit 10 recognizes the tissue of the subject by analyzing the ultrasound image U generated by the image generation unit 6. The tissue recognition unit 10 recognizes, as the tissue of the subject, at least one of the body surface S, blood vessels of a vein B1 and an artery B2, or subcutaneous anatomical structures other than the blood vessels of the subject as illustrated in FIG. 4, for example. Here, the anatomical structures include, for example, nerves and muscles. The tissue recognition unit 10 can recognize the tissue of the subject from the ultrasound image U by using, for example, a known algorithm such as template matching, a machine learning method, a general image recognition method using deep learning or the like.

Here, in FIG. 4, the ultrasound image U including the cross sections of the vein B1 and the artery B2 is exemplified, but instead of the cross sections of the vein B1 and the artery B2, longitudinal cross sections of the vein B1 and the artery B2 may be included in the ultrasound image U. The cross sections of the vein B1 and the artery B2 refer to cut sections of the vein B1 and the artery B2 by a plane orthogonal to a traveling direction of the vein B1 and the artery B2, and the longitudinal cross sections of the vein B1 and the artery B2 refer to cut sections of the vein B1 and the artery B2 along the traveling direction of the vein B1 and the artery B2.

In a case where the thickness of the gel layer G calculated by the gel layer thickness calculation unit 9 is equal to or less than a thickness threshold value, the press state determination unit 11 determines the press state of the ultrasound probe 21 against the body surface S of the subject on the basis of a shape change of the tissue recognized by the tissue recognition unit 10. In this case, the press state determination unit 11 calculates a shape change degree representing the shape change of the recognized tissue on the basis of the recognition result of the tissue by the tissue recognition unit 10, and determines that the body surface S of the subject is pressed by the ultrasound probe 21 in a case where the calculated shape change degree exceeds a shape change degree threshold value. Here, the value of the shape change degree is increased as the deformation of the tissue of the subject is large, and the value of the shape change degree is decreased as the deformation of the tissue of the subject is small.

Figure 5:
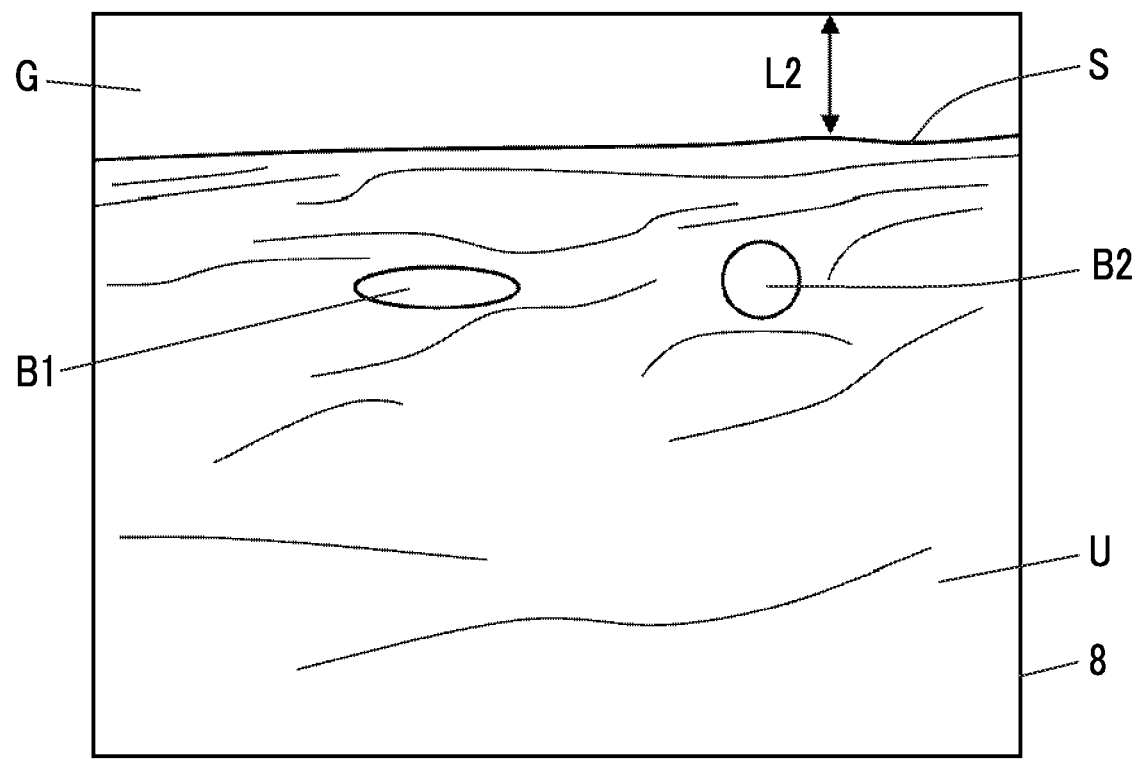
FIG. 5 is a schematic diagram of an ultrasound image in a state where the body surface of the subject is pressed by the ultrasound probe, in the first embodiment of the present invention.

For example, as the shape change degree, a change rate of the diameter of a blood vessel in the depth direction can be used. Here, the change rate of the diameter of the blood vessel in the depth direction can be calculated by subtracting a ratio of the diameter of the blood vessel in the depth direction in the current ultrasound image U to the diameter of the blood vessel in the depth direction in the ultrasound image U that is a reference for the ultrasound diagnosis, from 1. For example, in the reference ultrasound image U generated in the early stage of the ultrasound diagnosis, the gel layer G has the thickness L1 greater than the thickness threshold value and the cross section of the vein B1 has a substantially circular shape as illustrated in FIG. 4, and in the current ultrasound image U, the gel layer G has a thickness L2 equal to or less than the thickness threshold value and the cross section of the vein B1 is deformed to collapse in the depth direction as illustrated in FIG. 5. In a case where the thickness L2 of the gel layer G is equal to or less than the thickness threshold value and the change rate of the diameter of the vein B1, which is calculated on the basis of the vein B1 in the reference ultrasound image U and the vein B1 in the current ultrasound image U, is equal to or greater than the shape change degree threshold value, the press state determination unit 11 can determine that the body surface S of the subject is pressed by the ultrasound probe 21.

Here, it is known that the artery B2 is unlikely to be deformed by external pressure. Therefore, in a case where the shape change of the blood vessel is used for determining the press state of the ultrasound probe 21 against the body surface S of the subject, it is more useful for the press state determination unit 11 to use the shape change of the vein B1 rather than the shape change of the artery B2.

Figure 6:
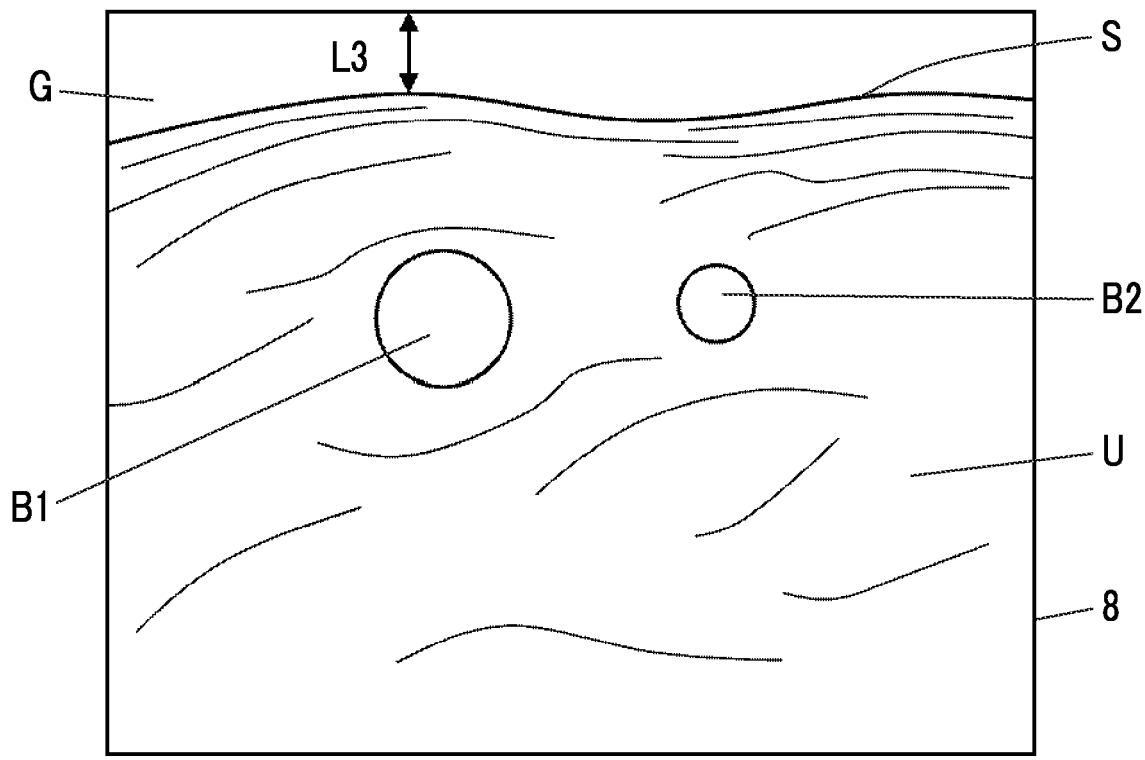
FIG. 6 is a schematic diagram of an ultrasound image in which a thickness of the gel layer is equal to or less than the thickness threshold value, in the first embodiment of the present invention.

In a case where the thickness of the gel layer G is equal to or less than the thickness threshold value and the calculated shape change degree is equal to or less than the shape change degree threshold value, the press state determination unit 11 determines that the body surface S of the subject is not pressed by the ultrasound probe 21. For example, in a case where the ultrasound image U representing a state in which the gel layer G has the thickness L1 greater than the thickness threshold value and the cross section of the vein B1 has a substantially circular shape as illustrated in FIG. 4 is used as the reference, in the current ultrasound image U, even when the gel layer G has a thickness L3 equal to or less than the thickness threshold value, as long as the change rate of the diameter of the vein B1 is equal to or less than the shape change degree threshold value as illustrated in FIG. 6, the press state determination unit 11 can determine that the body surface S of the subject is not pressed by the ultrasound probe 21.

Further, in a case where the thickness of the gel layer G calculated by the gel layer thickness calculation unit 9 is greater than the thickness threshold value, the press state determination unit 11 determines that an appropriate procedure is performed by the operator and the body surface S of the subject is not pressed by the ultrasound probe 21 without determining the press state, and thus the press state determination unit 11 does not determine the press state of the ultrasound probe 21.

By the way, in general, it is known that the gel layer applied to the body surface of the subject gradually becomes thinner in a case where the ultrasound probe is moved on the gel layer by the operator even in a state where the ultrasound probe does not press the body surface of the subject.

Thus, in a case where the press state determination unit 11 determines that the body surface S of the subject is pressed, the notification unit 12 instructs the operator to stop the pressing by the ultrasound probe 21, and in a case where the press state determination unit 11 determines that the body surface S of the subject is not pressed, the notification unit 12 instructs the operator to replenish the gel of the gel layer G.

Figure 7:
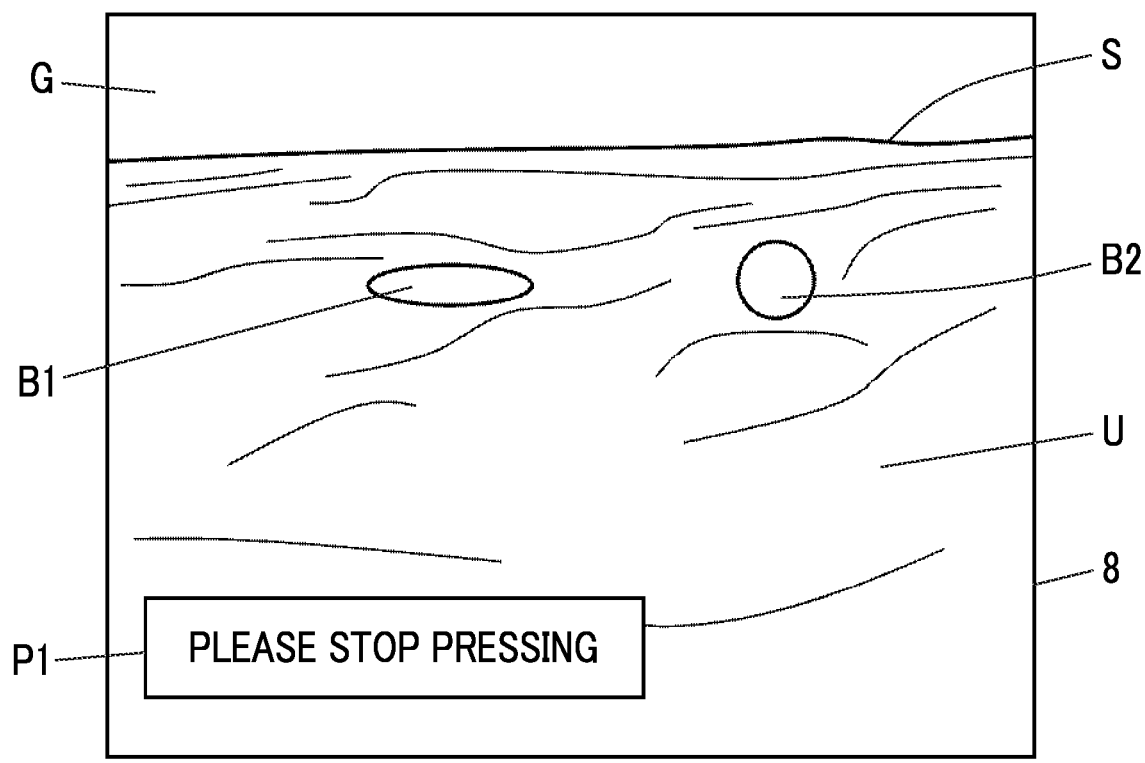
FIG. 7 is a schematic diagram illustrating an instruction to stop the pressing by the ultrasound probe, which is displayed on a display device in the first embodiment of the present invention.
Figure 8:
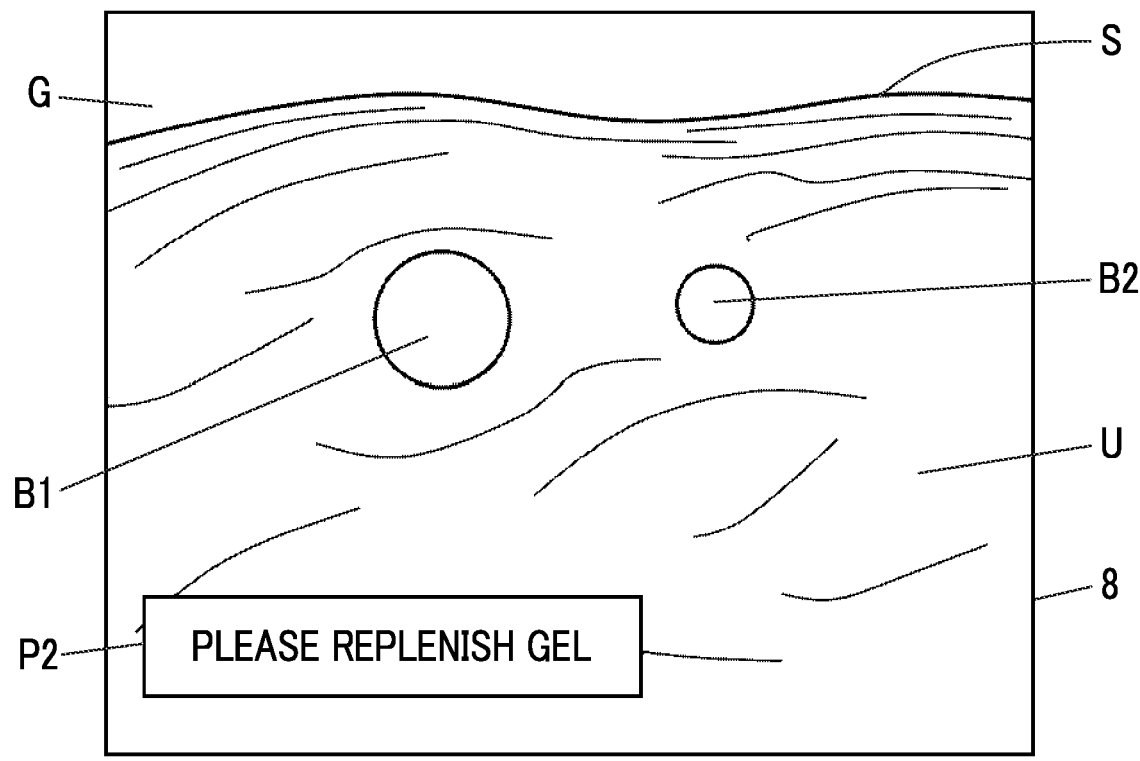
FIG. 8 is a schematic diagram illustrating an instruction to replenish a gel, which is displayed on the display device in the first embodiment of the present invention.

For example, the press state determination unit 11 can instruct the operator to stop the pressing by the ultrasound probe 21 by causing the display device 8 to display an instruction panel P1 including text "please stop the pressing" together with the ultrasound image U as illustrated in FIG. 7. For example, the press state determination unit 11 can instruct the operator to replenish the gel of the gel layer G by causing the display device 8 to display an instruction panel P2 including text "please replenish the gel" together with the ultrasound image U as illustrated in FIG. 8.

The device control unit 13 controls each unit of the ultrasound diagnostic apparatus 1 on the basis of a program stored in advance in the storage unit 15 or the like and the operator's input operation through the input device 14.

The display control unit 7 causes the display device 8 to display the ultrasound image U and the instruction to the operator by the notification unit 12 by performing predetermined processing on the ultrasound image U generated by the image generation unit 6, information or the like representing the instruction to the operator by the notification unit 12, and the like under the control of the device control unit 13.

The display device 8 is for displaying the ultrasound image U, the instruction to the operator by the notification unit 12, and the like under the control of the display control unit 7, and includes a display device such as a liquid crystal display (LCD), or an organic electroluminescence (EL) display.

The input device 14 is for the operator to perform an input operation, and can be configured to comprise a keyboard, a mouse, a trackball, a touchpad, a touch panel, and the like.

The storage unit 15 stores a control program and the like of the ultrasound diagnostic apparatus 1, and recording media such as a flash memory, a hard disk drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), a server, or the like can be used.

The processor 22 having the image generation unit 6, the display control unit 7, the gel layer thickness calculation unit 9, the tissue recognition unit 10, the press state determination unit 11, the notification unit 12, and the device control unit 13 is configured by a central processing unit (CPU) and a control program for causing the CPU to execute various kinds of processing, but the processor 22 may be configured by using a field programmable gate array (FPGA), a digital signal processor (DSP), an application specific integrated circuit (ASIC), a graphics processing unit (GPU), or other integrated circuits (IC) or may be configured by a combination thereof.

In addition, the image generation unit 6, the display control unit 7, the gel layer thickness calculation unit 9, the tissue recognition unit 10, the press state determination unit 11, the notification unit 12, and the device control unit 13 of the processor 22 can also be configured by being integrated partially or entirely into one CPU or the like.

Figure 9:
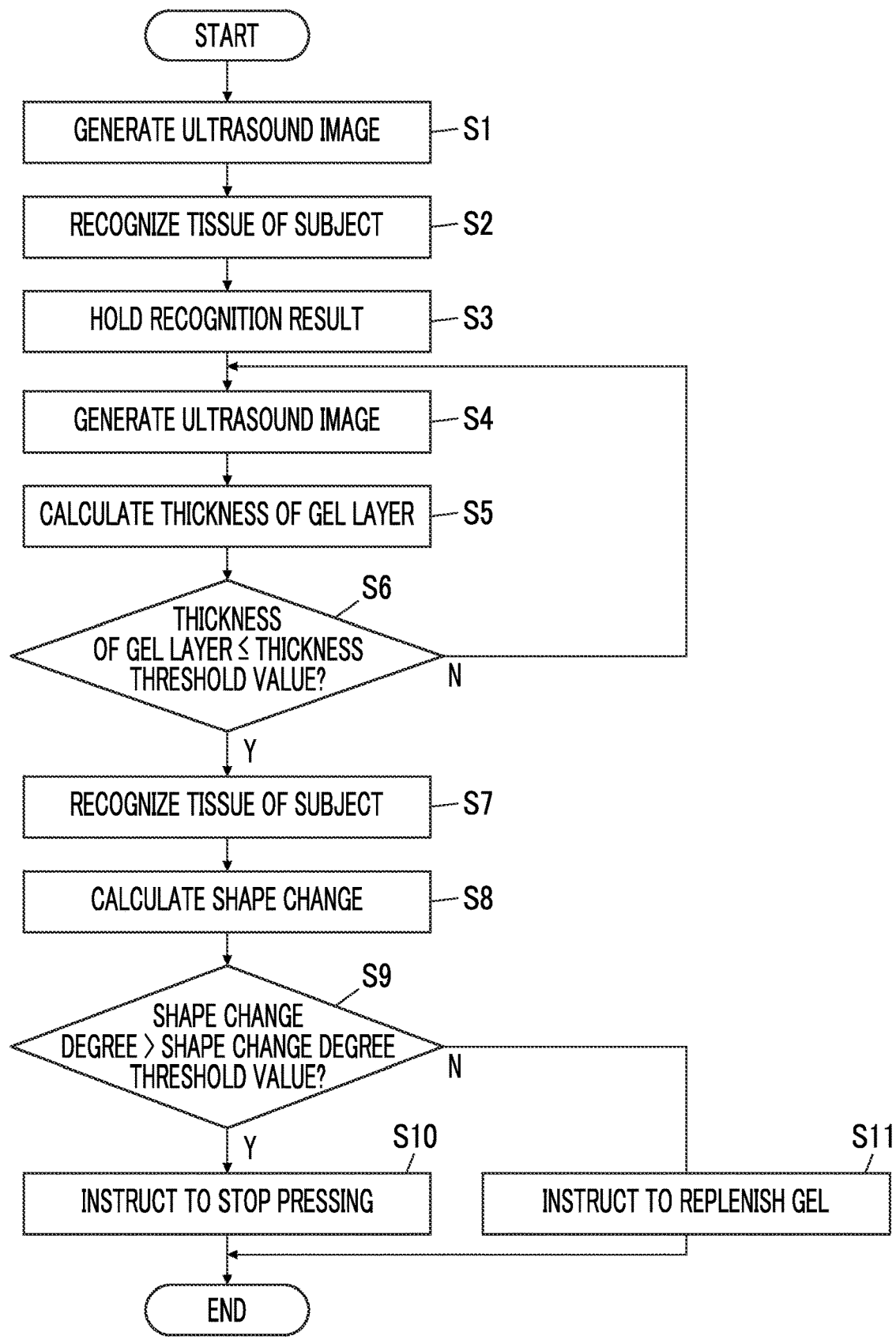
FIG. 9 is a flowchart illustrating an operation of the ultrasound diagnostic apparatus according to the first embodiment of the present invention.

In the following, the operation of the ultrasound diagnostic apparatus 1 in the first embodiment will be described in detail using the flowchart illustrated in FIG. 9.

First, in Step S1, a sufficient amount of gel layer G is applied to the body surface S of the subject by the operator, and the ultrasound probe 21 is brought into contact with the applied gel layer G. In such a state, the ultrasound image U in which the body surface S of the subject to which the gel layer G is applied and the tissue present in the subcutaneous portion are imaged is generated, and the generated ultrasound image U is displayed on the display device 8. In this case, an ultrasound beam is transmitted into the subject from the plurality of transducers of the transducer array 2 according to the drive signal from the transmission circuit 3, the reception signal is output to the reception circuit 4 from each transducer which has received the ultrasound echo from the subject. The reception signal received by the reception circuit 4 is amplified in the amplification unit 23, is subjected to the AD conversion in the AD conversion unit 24, and is phased and added in the beam former 25, and thereby the sound ray signal is generated. The sound ray signal is subjected to the envelope detection processing by the signal processing unit 26 to become the B-mode image signal in the image generation unit 6, and is output to the display control unit 7 via the DSC 27 and the image processing unit 28, and the ultrasound image U is displayed on the display device 8 under the control of the display control unit 7 as illustrated in FIG. 4.

Next, in Step S2, the tissue recognition unit 10 recognizes the tissue of the subject by analyzing the ultrasound image U generated in Step S1. For example, the tissue recognition unit 10 can recognize the vein B1 as the tissue of the subject, as illustrated in FIG. 4. In this case, the tissue recognition unit 10 can recognize the vein B1 by using, for example, a known algorithm such as template matching, a machine learning method, a general image recognition method using deep learning or the like.

In subsequent Step S3, the press state determination unit 11 holds recognition result of Step S2, for example, the information representing the shape of the vein B1, as the reference for determining the shape change thereof.

Similar to Step S1, in Step S4, the ultrasound image U is newly generated, and the generated ultrasound image U is displayed on the display device 8.

In Step S5, the gel layer thickness calculation unit 9 calculates the thickness of the gel layer G by analyzing the ultrasound image U generated in Step S4. For example, as illustrated in FIG. 4, the gel layer thickness calculation unit 9 recognizes the body surface S of the subject in the ultrasound image U, and calculates the shallowest position of the ultrasound image U in the depth direction of the ultrasound image U, that is, the shortest length from the upper end portion of the ultrasound image U to the body surface S, as the thickness L1 of the gel layer G. More specifically, the gel layer thickness calculation unit 9 can recognize a place where the brightness change in the depth direction from the shallow portion of the ultrasound image U is greater than a certain value, as the body surface S. The gel layer thickness calculation unit 9 can recognize the body surface S on the ultrasound image U by using, for example, a known algorithm such as template matching, a machine learning method, a general image recognition method using deep learning or the like.

In Step S6, the press state determination unit 11 determines whether the thickness of the gel layer G calculated in Step S5 is equal to or less than a predetermined thickness threshold value. In a case where the press state determination unit 11 determines that the thickness of the gel layer G is greater than the thickness threshold value, it is determined that it is not necessary to determine the press state of the ultrasound probe 21, the processing returns to Step S4, and the ultrasound image U is newly generated. The thickness of the gel layer G is calculated in Step S5 on the basis of the ultrasound image U generated in this manner, and the processing proceeds to Step S6.

In Step S6, in a case where it is determined that the thickness of the gel layer G is equal to or less than the thickness threshold value, the processing proceeds to Step S7. Similar to Step S2, in Step S7, the tissue of the subject such as the vein B1 is recognized by analyzing the ultrasound image U generated in Step S4.

In Step S8, the press state determination unit 11 calculates the shape change degree relating to the tissue of the subject recognized in Step S7. For example, in a case where the shape of the vein B1 is held in Step S3, the press state determination unit 11 can calculate, as the shape change degree, the change rate of the diameter of the vein B1 by subtracting a ratio of the diameter of the vein B1, which is recognized in Step S7, in the depth direction to the diameter of the vein B1, of which the shape is held in Step S3, in the depth direction, from 1.

In subsequent Step S9, the press state determination unit 11 determines whether the shape change degree calculated in Step S8 exceeds the shape change degree threshold value. For example, as illustrated in FIG. 5, in a case where the cross section of the vein B1 recognized in Step S7 collapses in the depth direction of the ultrasound image U and the shape change degree exceeds the shape change degree threshold value by using, as the shape change degree, the change rate of the diameter of the vein B1 calculated on the basis of the vein B1 recognized in Step S7 and the vein B1 of which the shape is held in Step S3, it is determined that the body surface S of the subject is pressed by the ultrasound probe 21, and the processing proceeds to Step S10.

In Step S10, the notification unit 12 instructs the operator to stop the pressing by the ultrasound probe 21. For example, the notification unit 12 can instruct the operator to stop the pressing by the ultrasound probe 21 by causing the display device 8 to display the instruction panel P1 including text "please stop the pressing" together with the ultrasound image U as illustrated in FIG. 7. In a case where the processing of Step S10 is completed in this manner, the operation of the ultrasound diagnostic apparatus 1 is ended.

As illustrated in FIG. 6, in a case where the cross section of the vein B1 has a substantially circular shape and the press state determination unit 11 determines in Step S9 that the shape change degree relating to the vein B1 is equal to or less than the shape change degree threshold value, it is determined that the body surface S of the subject is not pressed by the ultrasound probe 21, and the processing proceeds to Step S11.

In Step S11, the notification unit 12 instructs the operator to replenish the gel of the gel layer G. For example, the notification unit 12 can instruct the operator to replenish the gel of the gel layer G by causing the display device 8 to display the instruction panel P2 including text "please replenish the gel" together with the ultrasound image U as illustrated in FIG. 8. In a case where the instruction of Step S11 is completed in this manner, the operation of the ultrasound diagnostic apparatus 1 is ended.

As described above, with the ultrasound diagnostic apparatus 1 according to the first embodiment of the present invention, the thickness of the gel layer G applied to the body surface S of the subject is calculated and the tissue of the subject is recognized by analyzing the ultrasound image U, and the press state of the ultrasound probe 21 against the body surface S of the subject is determined on the basis of both the calculated thickness of the gel layer G and the shape change of the tissue of the subject. Therefore, for example, it is possible to prevent erroneous determination that the body surface S of the subject is pressed by the ultrasound probe 21 even when the ultrasound probe 21 does not press the body surface S of the subject, due to the thinning of the gel layer G. In this manner, with the ultrasound diagnostic apparatus 1 according to the first embodiment of the present invention, it is possible to accurately determine the press state of the ultrasound probe 21 against the body surface S of the subject.

Since the instruction to stop the pressing by the ultrasound probe 21 or the instruction to replenish the gel of the gel layer G is given to the operator by the notification unit 12 according to the determination result of the press state determination unit 11, the operator can perform an appropriate procedure so as not to press the body surface S of the subject by the ultrasound probe 21. Therefore, with the ultrasound diagnostic apparatus 1 of the first embodiment of the present invention, it is possible to improve the accuracy of the ultrasound diagnosis.

In Step S1 to Step S3, after the operation start of the ultrasound diagnostic apparatus 1, the tissue of the subject is recognized on the basis of the ultrasound image U of the subject which is generated for the first time, and the recognition result is held, but the ultrasound image used here is not limited to the newly generated image, and may be, for example, the ultrasound image obtained in the past diagnosis. For example, the ultrasound diagnostic apparatus 1 comprises an image memory (not illustrated) that stores the ultrasound image obtained in the past diagnosis, and the past ultrasound image can be read from the image memory instead of generating the ultrasound image U in Step S1. In this case, by analyzing the read past ultrasound image in Step S2, the tissue of the subject included in the ultrasound image is recognized, and the recognition result is held in Step S3.

The ultrasound image in which the recognition of the tissue is to be performed in Step S2 may be an ultrasound image obtained by imaging the inside of a subject other than the subject that is the current target of the ultrasound diagnosis as long as the site of the imaging target is the same, and may be an ultrasound image obtained by imaging the inside of a so-called ultrasound phantom. Even in such a case, as long as the site of the imaging target is the same, the body surface and the subcutaneous anatomical structures are not changed significantly depending on the subject, and therefore, it is possible to accurately determine the press state of the ultrasound probe 21 against the body surface S of the subject by using the ultrasound diagnostic apparatus 1 according to the first embodiment of the present invention.

Further, it has been described that the gel layer thickness calculation unit 9 calculates the shortest length from the upper end portion of the ultrasound image U to the body surface S of the subject as the thickness L1 of the gel layer G, but for example, an average value of the lengths from the upper end portion of the ultrasound image U to the body surface S of the subject can be calculated as the thickness of the gel layer G. In this case, the gel layer thickness calculation unit 9 can calculate the average value of the lengths from the upper end portion of the ultrasound image U to the body surface S of the subject by calculating the area of a region from the upper end portion of the ultrasound image U to the body surface S of the subject, and dividing the calculated area by the width of the ultrasound image U in a direction orthogonal to the depth direction.

The change rate of the diameter of the blood vessel in the depth direction is exemplified as the shape change degree, but the shape change degree is not limited thereto as long as the value represents a change in the shape of the tissue of the subject. For example, as the shape change degree, a change rate of an area of the blood vessel can be used, which is calculated by subtracting a ratio of the area of the cross section of the blood vessel in the current ultrasound image U to the area of the cross section of the blood vessel in the reference ultrasound image U, from 1. Further, for example, the flatness of the cross section of the blood vessel can be used as the shape change degree. The flatness is calculated by subtracting a ratio of the diameter of the blood vessel in the depth direction to the diameter of the blood vessel in a direction orthogonal to the depth direction in the ultrasound image U, from 1. The flatness has a value closer to 0 as the cross section of the blood vessel is closer to a perfect circle, and has a value closer to 1 as the cross section of the blood vessel collapses in the depth direction.

The reciprocal of the circularity of the cross section of the blood vessel, the reciprocal of the similarity degree between the cross section of the blood vessel and the perfect circle, and the like can be used as the shape change degree.

The press state determination unit 11 uses the shape change of the cross section of the blood vessel for determining the press state of the ultrasound probe 21, but without being limited to using the shape change of the cross section of the blood vessel, for example, the press state determination unit 11 can use the shape change of the longitudinal cross section of the blood vessel for determining the press state of the ultrasound probe 21. In this case, the press state determination unit 11 can calculate, as a blood vessel diameter, a distance between a vascular wall positioned on a shallow portion and a vascular wall positioned on a deep portion in the depth direction, and can use, as the shape change degree, the change rate of the blood vessel diameter calculated by subtracting a ratio of the blood vessel diameter in the current ultrasound image U to the blood vessel diameter in the reference ultrasound image U, from 1.

In addition, for example, the press state determination unit 11 can also use the shape change of the subcutaneous anatomical structure such as muscles and nerves for determining the press state of the ultrasound probe 21. For example, the press state determination unit 11 can measure the thickness of the muscles, nerves, and the like of the subject recognized by the tissue recognition unit 10 in the depth direction, calculates the change rate of the thickness of the muscles, nerves, and the like by subtracting a ratio of the thickness of the muscles, nerves, and the like in the depth direction in the current ultrasound image U to the thickness of the muscles, nerves, and the like in the depth direction in the reference ultrasound image U, from 1, and use the calculated change rate for determining the press state of the ultrasound probe 21.

The muscles, subcutaneous tissues, and the like of the subject generally have a layered structure, and in a case where the body surface S of the subject is pressed by the ultrasound probe 21, each layer of the muscles, subcutaneous tissues, and the like is compressed in the depth direction to become thin. Since the layered structure of the muscles, subcutaneous tissues, and the like is depicted as a repeating pattern in the ultrasound image U, a spatial frequency of the layered structure of the muscles, subcutaneous tissues, and the like in the depth direction of the ultrasound image U is considered to be increased as the muscles, subcutaneous tissues, and the like are compressed in the depth direction. Therefore, the press state determination unit 11 can calculate the spatial frequency of the image of the muscles, nerves, and the like of the subject recognized by the tissue recognition unit 10, and calculate, as the shape change rate, a ratio of the spatial frequency of the muscles, nerves, and the like in the depth direction in the current ultrasound image U to the spatial frequency of the muscles, nerves, and the like in the depth direction in the reference ultrasound image U.

As illustrated in FIG. 4, in a case where the body surface S of the subject is not pressed by the ultrasound probe 21, the tissue such as the vein B1 is present in the subcutaneous portion, so that the body surface S of the subject appears curved in the ultrasound image U, but as illustrated in FIG. 5, in a case where the body surface S of the subject is pressed by the ultrasound probe 21, the tissue such as the vein B1 is compressed in the depth direction, so that the body surface S of the subject appears substantially linearly in the ultrasound image U. Therefore, for example, the press state determination unit 11 can use the shape change of the body surface S of the subject for determining the press state of the ultrasound probe 21. For example, the press state determination unit 11 can approximate the shape of the body surface S of the subject with a curve, and calculate the reciprocal of the number of inflection points of the curve as the shape change degree. The press state determination unit 11 can obtain a similarity degree or the like between a straight line and a curve that approximates the body surface S of the subject to calculate a linearity degree representing how close the curve is to the straight line, and calculate the calculated linearity degree as the shape change degree.

Further, the press state determination unit 11 can use a predetermined value as the shape change degree threshold value.

For example, in a case where the shape change of the blood vessel is used for determining the press state of the ultrasound probe 21 by the press state determination unit 11, the press state determination unit 11 can set the shape change degree threshold value such that the value is increased as the position of the blood vessel recognized by the tissue recognition unit 10 is shallower. For example, the press state determination unit 11 can store a reference value of the distance from the body surface S of the subject to the vein B1 in the depth direction and the shape change degree threshold value corresponding to the distance, and set the shape change degree threshold value such that the shape change degree threshold value is increased as the distance from the body surface S of the subject to the vein B1 in the depth direction is shorter than the reference value and the shape change degree threshold value is decreased as the distance from the body surface S of the subject to the vein B1 in the depth direction is longer than the reference value.

For example, in a case where the vein B1 is located at a shallow position, that is, a position close to the body surface S of the subject, the influence of the pressing by the ultrasound probe 21 is large, and the shape of the vein B1 is likely to be changed as compared with a case where the vein B1 is located at a deep position, that is, a position far from the body surface S of the subject. Therefore, by setting the shape change degree threshold value according to the depth of the blood vessel such as the vein B1, the shape change degree threshold value can be set according to the ease of the shape change of the blood vessel according to the depth, and the press state of the ultrasound probe 21 against the body surface S of the subject can be more accurately determined.

In a case where a joint or the like where a bone is present near the subcutaneous portion of the subject is pressed from the outside, the tissue between the bone and the body surface S is easily deformed. Thus, for example, the press state determination unit 11 can set the shape change degree threshold value according to the site of the imaging target of the subject. For example, the press state determination unit 11 can store a value determined for each site of the subject, and can set the value corresponding to the input site as the shape change degree threshold value in a case where information representing the site of the imaging target such as a joint is input through the input device 14 by the operator. Although not illustrated, the ultrasound diagnostic apparatus 1 can include a site determination unit that determines a site of the subject imaged on the basis of the tissue of the subject recognized by the tissue recognition unit 10. In this case, the press state determination unit 11 can set a value corresponding to the site determined by the site determination unit as the shape change degree threshold value.

The press state determination unit 11 uses a predetermined value as the threshold value of the thickness of the gel layer G, but the threshold value can be set on the basis of the thickness of the gel layer G calculated by the gel layer thickness calculation unit 9.

For example, the press state determination unit 11 can set a value obtained by multiplying the thickness of the gel layer G, which is first calculated by the gel layer thickness calculation unit 9, by a certain ratio such as 30% as the threshold value after the ultrasound diagnosis is started. In general, the gel used as the gel layer to be applied to the subject has various viscosities depending on the type. Therefore, by setting the value obtained by multiplying the initial value of the thickness of the gel layer G by a certain ratio as the thickness threshold value, an appropriate thickness threshold value can be set according to the gel constituting the gel layer G, and the press state of the ultrasound probe 21 against the body surface S of the subject can be more accurately determined.

The shape change degree is described such that the value is increased as the deformation of the tissue of the subject is greater and the value is decreased as the deformation of the tissue of the subject is smaller. However, instead of the shape change degree, an index of which the value is decreased as the deformation of the tissue of the subject is greater and the value is increased as the deformation of the tissue of the subject is smaller can be used. As such an index, for example, a ratio of the diameter of the blood vessel in the depth direction in the current ultrasound image U to the diameter of the blood vessel in the depth direction in the ultrasound image U that is a reference for the ultrasound diagnosis, a ratio of the area of the blood vessel in the current ultrasound image U to the area of the blood vessel in the ultrasound image U that is a reference for the ultrasound diagnosis, a ratio of the diameter of the blood vessel in the depth direction to the diameter of the blood vessel in a direction orthogonal to the depth direction in the ultrasound image U, the circularity of the cross section of the blood vessel, the similarity degree between the cross section of the blood vessel and the perfect circle, or the like can be used. In this case, for example, in a case where the thickness of the gel layer G calculated by the gel layer thickness calculation unit 9 is equal to or less than the thickness threshold value and the calculated index is equal to or less than a certain threshold value, the press state determination unit 11 can determine that the body surface S of the subject is pressed by the ultrasound probe 21.

As illustrated in FIGS. 7 and 8, it has been described that the instruction panels P1 and P2 representing the instruction to the operator are displayed on the display device 8 by the notification unit 12, but the method for the instruction is not particularly limited as long as the instruction is given to the operator. For example, the ultrasound diagnostic apparatus 1 comprises a speaker (not illustrated) that emits voice, and as the instruction to the operator, voice such as "please stop the pressing" and "please replenish the gel" can be emitted from the speaker by the notification unit 12.

Further, the transmission and reception circuit 5 is included in the ultrasound probe 21, but may be provided outside the ultrasound probe 21. In such a case, similarly to the case where the transmission and reception circuit 5 is included in the ultrasound probe 21, the transmission and reception circuit 5 can cause the transducer array 2 to transmit the ultrasound beam toward the subject, and process the reception signal output from the transducer array 2 that has received the ultrasound echo from the subject.

Further, the beam former 25 that performs so-called reception focusing processing is included in the reception circuit 4, but can be included in the image generation unit 6, for example. Also in this case, similarly to the case where the beam former 25 is included in the reception circuit 4, the ultrasound image U is generated by the image generation unit 6.

Second Embodiment

The ultrasound diagnostic apparatus 1 of the first embodiment has the configuration in which the display device 8, the input device 14, and the ultrasound probe 21 are directly connected to the processor 22, but, for example, the display device 8, the input device 14, the ultrasound probe 21, and the processor 22 can be indirectly connected to each other via the network.

Figure 10:
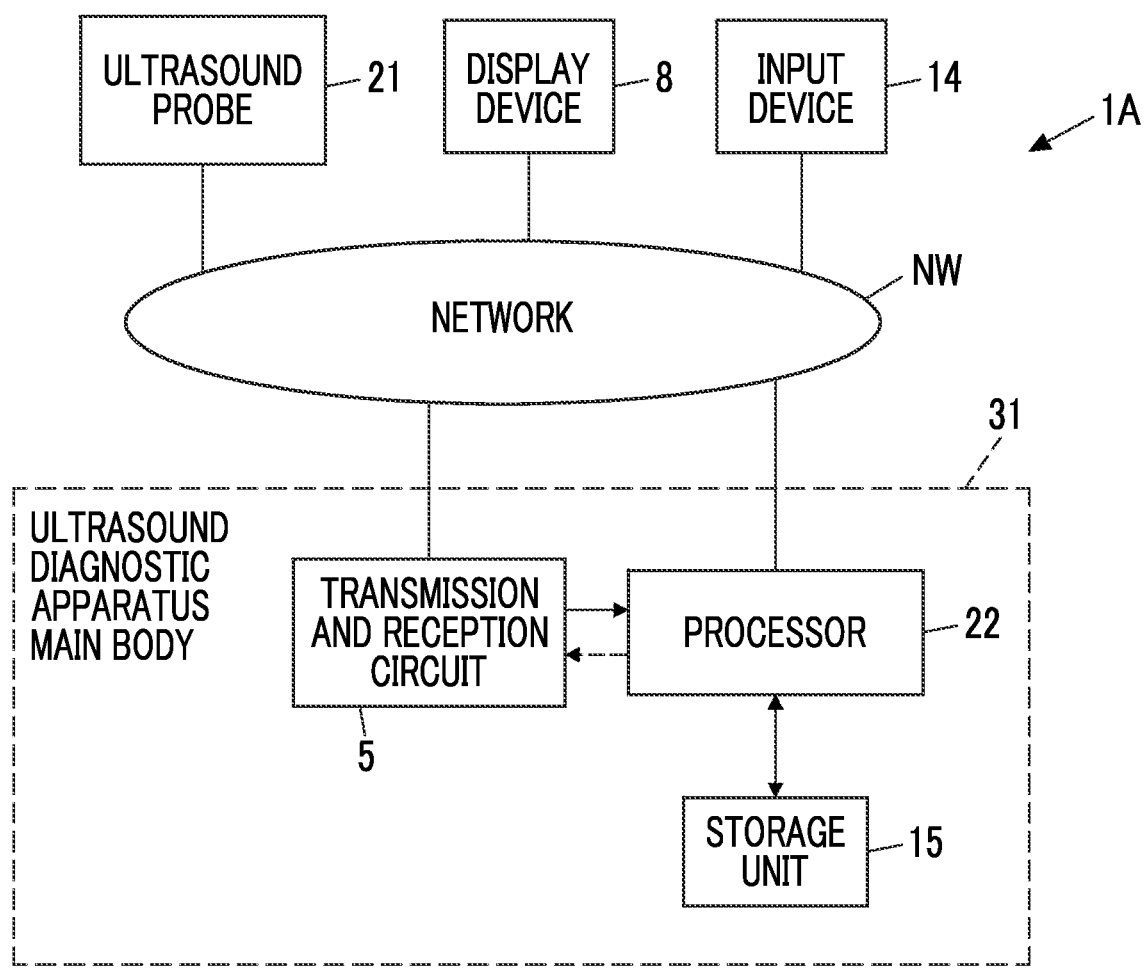
FIG. 10 is a block diagram illustrating a configuration of an ultrasound diagnostic apparatus according to a second embodiment of the present invention.

As illustrated in FIG. 10, in an ultrasound diagnostic apparatus 1A in a second embodiment, the display device 8, the input device 14, and the ultrasound probe 21 are connected to an ultrasound diagnostic apparatus main body 31 via a network NW. The ultrasound diagnostic apparatus main body 31 is obtained by excluding the display device 8, the input device 14, and the ultrasound probe 21 in the ultrasound diagnostic apparatus 1 of the first embodiment illustrated in FIG. 1, and is constituted by the transmission and reception circuit 5, the storage unit 15, and the processor 22.

Even in a case where the ultrasound diagnostic apparatus 1A has such a configuration, similarly to the ultrasound diagnostic apparatus 1 of the first embodiment, the thickness of the gel layer G applied to the body surface S of the subject is calculated and the tissue of the subject is recognized by analyzing the ultrasound image U, and the press state of the ultrasound probe 21 against the body surface S of the subject is determined on the basis of both the calculated thickness of the gel layer G and the shape change of the tissue of the subject. Therefore, for example, it is possible to prevent erroneous determination that the body surface S of the subject is pressed by the ultrasound probe 21 even when the ultrasound probe 21 does not press the body surface S of the subject, due to the thinning of the gel layer G. In this manner, similarly to the ultrasound diagnostic apparatus 1 of the first embodiment, with the ultrasound diagnostic apparatus 1A according to the second embodiment of the present invention, it is possible to accurately determine the press state of the ultrasound probe 21 against the body surface S of the subject.

Since the instruction to stop the pressing by the ultrasound probe 21 or the instruction to replenish the gel of the gel layer G is given to the operator by the notification unit 12 according to the determination result of the press state determination unit 11, the operator can perform an appropriate procedure so as not to press the body surface S of the subject by the ultrasound probe 21. Therefore, similarly to the ultrasound diagnostic apparatus 1A of the first embodiment, with the ultrasound diagnostic apparatus 1 of the second embodiment of the present invention, it is possible to improve the accuracy of the ultrasound diagnosis.

Further, since the display device 8, the input device 14, and the ultrasound probe 21 are connected to the ultrasound diagnostic apparatus main body 31 via the network NW, the ultrasound diagnostic apparatus main body 31 can be used as a so-called remote server. Thereby, for example, since the operator can perform a diagnosis of the subject by preparing the display device 8, the input device 14, and the ultrasound probe 21 at the operator's hand, it is possible to improve the convenience in a case of the ultrasound diagnosis.

Further, in a case where a portable thin computer, for example, a so-called tablet, is used as the display device 8 and the input device 14, it is possible for the operator to more easily perform the ultrasound diagnosis of the subject, and it is possible to further improve the convenience in a case of the ultrasound diagnosis.

The display device 8, the input device 14, and the ultrasound probe 21 are connected to the ultrasound diagnostic apparatus main body 31 via the network NW, but in this case, the display device 8, the input device 14, and the ultrasound probe 21 may be connected to the network NW in a wired manner or in a wireless manner.

EXPLANATION OF REFERENCES 1, 1A: ultrasound diagnostic apparatus
2: transducer array
3: transmission circuit
4: reception circuit
5: transmission and reception circuit
6: image generation unit
7: display control unit
8: display device
9: gel layer thickness calculation unit
10: tissue recognition unit
11: press state determination unit
12: notification unit
13: device control unit
14: input device
15: storage unit
21: ultrasound probe
22: processor
23: amplification unit
24: AD conversion unit
25: beam former
26: signal processing unit
27: DSC
28: image processing unit
31: ultrasound diagnostic apparatus main body
B1: vein
B2: artery
G: gel layer
L1, L2, L3: thickness
NW: network
P1, P2: instruction panel
S: body surface
U: ultrasound image

What is claimed is:

1. An ultrasound diagnostic apparatus that acquires an ultrasound image by bringing an ultrasound probe into contact with a gel layer which is applied to a body surface of a subject, the ultrasound diagnostic apparatus comprising:
the ultrasound probe including at least a transducer array;
a transmission and reception circuit that causes the transducer array to transmit an ultrasound beam toward the subject, and processes a reception signal output from the transducer array that has received an ultrasound echo from the subject to generate a sound ray signal;
a processor configured to
generate the ultrasound image based on the sound ray signal generated by the transmission and reception circuit,
calculate the thickness of the gel layer by analyzing the ultrasound image,
upon being calculated the thickness of the gel layer which is equal or less than a thickness threshold value,
recognize a tissue of the subject by analyzing the ultrasound image,
determine a shape change degree representing a shape change of the tissue which is recognized, and
when the shape change degree exceeds a shape change degree threshold value,
determine that the body surface of the subject is pressed by the ultrasound probe, and
instruct an operator to stop pressing by the ultrasound probe,
when the shape change degree of the tissue which is recognized is equal to or less than the shape change degree threshold value,
determine that the body surface of the subject is not pressed by the ultrasound probe, and
instruct the operator to replenish a gel of the gel layer.

2. The ultrasound diagnostic apparatus according to claim 1,
wherein the processor is further configured to recognize at least one of the body surface, a blood vessel, or a subcutaneous anatomical structure other than the blood vessel, as the tissue.

3. The ultrasound diagnostic apparatus according to claim 2,
wherein the thickness threshold value is a predetermined value.

4. The ultrasound diagnostic apparatus according to claim 1,
wherein the processor is further configured to
recognize a blood vessel as the tissue, and
set the shape change degree threshold value such that the shape change degree threshold value is increased as a position of the blood vessel which is recognized is shallower.

5. The ultrasound diagnostic apparatus according to claim 4,
wherein the thickness threshold value is a predetermined value.

6. The ultrasound diagnostic apparatus according to claim 1,
wherein the thickness threshold value is a predetermined value.

7. The ultrasound diagnostic apparatus according to claim 1,
wherein the processor is further configured to set a value obtained by multiplying the thickness of the gel layer, which is first calculated, by a certain ratio as the thickness threshold value.

8. A control method of an ultrasound diagnostic apparatus, the control method comprising:

causing a transducer array of an ultrasound probe brought into contact with a gel layer which is applied to a body surface of a subject to transmit an ultrasound beam toward the subject, and processing a reception signal output from the transducer array that has received an ultrasound echo from the subject to generate a sound ray signal;

generating, via a processor of the ultrasound diagnostic apparatus, an ultrasound image based on the generated sound ray signal;

calculating, via the processor, the thickness of the gel layer by analyzing the generated ultrasound image;

upon being calculated the thickness of the gel layer which is equal or less than a thickness threshold value, recognizing, via the processor, a tissue of the subject by analyzing the generated ultrasound image;

determining, via the processor, that a shape change degree representing a shape change of the tissue which is recognized is equal to or less than a shape change degree threshold value, and in response to determining that the shape change degree of the tissue is equal to or less than the shape change degree threshold, determining, via the processor, that the body surface of the subject is not pressed by the ultrasound probe; and instructing, via the processor, the operator to replenish a gel of the gel layer.

* * * * *